United States Patent
Moloney et al.

(10) Patent No.: US 7,034,129 B2
(45) Date of Patent: Apr. 25, 2006

(54) PROCESS FOR SURFACE FUNCTIONALSATION OF POLYMERIC SUBSTRATES USING DIARYL CARBENES AS REACTIVE INTERMEDIATES

(75) Inventors: Mark Gerard Moloney, Oxford (GB); Warren Ebenezer, Oxford (GB); Karim Awenat, Oxford (GB)

(73) Assignee: Isis Innovation Limited, Oxford (GB)

( * ) Notice: Subject to any disclaimer, the term of this patent is extended or adjusted under 35 U.S.C. 154(b) by 214 days.

(21) Appl. No.: 10/741,288

(22) Filed: Dec. 19, 2003

(65) Prior Publication Data

US 2004/0127691 A1  Jul. 1, 2004

Related U.S. Application Data

(63) Continuation of application No. 09/830,829, filed as application No. PCT/GB99/03629 on Nov. 3, 1999, now Pat. No. 6,699,527.

(51) Int. Cl.
*C07C 245/14* (2006.01)
(52) U.S. Cl. ..................................... 534/558
(58) Field of Classification Search ................. 534/558
See application file for complete search history.

(56) References Cited

U.S. PATENT DOCUMENTS

| | | | |
|---|---|---|---|
| 3,376,276 A | | 4/1968 | Morgan et al. |
| 4,309,453 A | | 1/1982 | Reiner et al. |
| 5,075,427 A | | 12/1991 | Kang et al. |
| 5,154,808 A | | 10/1992 | Miyasaka et al. |
| 5,587,464 A | * | 12/1996 | Kawahara et al. .......... 534/558 |

FOREIGN PATENT DOCUMENTS

| | | |
|---|---|---|
| CA | 812736 | 5/1969 |
| EP | 0 014 843 | 1/1972 |
| FR | 1500512 | 1/1968 |
| GB | 1344991 | 3/1970 |
| GB | 1344993 | 5/1970 |
| GB | 1412963 | 1/1972 |
| WO | WO-00/26180 | 5/2000 |

OTHER PUBLICATIONS

Vorotnikov, A.P. et al: "Formulation and conversion of biradicals in polymer matrixes during photodecomposition of diphenyldiazomethane in quasiclusters," *Chemical Abstracts* 116(3):530 (1992).
International Search Report, issued Feb. 16, 2000.
Braybrook, D.R. et al., "The preparation and reactivity of some photoactivable reactive dyes," *J. Photochecm. Photobiol. A: Chem.* 70:171-178 (1993).
Worley, S.D. et al., "Biocidal Polymers," *TRIP* 4(11):364-370 (1996).
Sun, G. et al., "Dressing to kill," *Chemistry & Industry* 658-661 (1999).

* cited by examiner

*Primary Examiner*—Fiona T. Powers
(74) *Attorney, Agent, or Firm*—Fulbright & Jaworski LLP

(57) ABSTRACT

A process for the surface functionalisation of a polymeric substrate, which process comprises:
 (a) contacting the substrate with a diarylcarbene precursor,
 (b) generating a carbene reactive intermediate from the diarylcarbene precursor so that it reacts with the substrate to functionalise the surface, and
 (c) further functionalising the activated substrate obtained in step (b).

5 Claims, No Drawings

PROCESS FOR SURFACE FUNCTIONALSATION OF POLYMERIC SUBSTRATES USING DIARYL CARBENES AS REACTIVE INTERMEDIATES

CROSS REFERENCE TO RELATED APPLICATION

This application is a continuation of Ser. No. 09/830,829 filed Aug. 21, 2001 now U.S. Pat. No. 6,699,527, which claimed priority from PCT/GB99/03629 filed Nov. 3, 1999.

The present invention relates to a process for the surface functionalisation of a polymeric substrate using diarylcarbenes as the reactive intermediates. The invention in particular relates to a process for the surface functionalisation, for example dyeing, of substrates such as cotton, a variety of plastics, polystyrene, nylon, controlled pore glass, silica, an ethylene polymer or polytetrafluoroethylene.

Dyestuffs which are used to colour natural and synthetic polymers, via covalent modification, most commonly rely upon the presence of highly reactive groups which have been coupled to the chromophoric species. Examples include the Procion and Gibacron range of dyes (which rely upon the reactivity of a chlorotriazinyl residue with nucleophilic residues on the substrate), the Remazol range of dyes (which rely on a vinylsulfonyl residue as a nucleophilic acceptor) and the Drimalon range of dyes (which contain an α-chloroacetyl residue as the reactive species). Modifications of these reactive entities have been developed, leading to other related dye classes (e.g. the Drimarenes and Reactones, which use a tetrachloropyrimidine reactive unit, and the Primazin dyes, which use an acrylamide residue). Each of these reactive classes of dye have preferred substrates, although all contain aromatic or vinylic groups which are particularly activated towards nucleophilic attack by suitable functionality on the substrate. Development of this type of strategy still continues. However, in addition to the requirement for nucleophilic functionality on the substrate (which would usually be hydroxyl or amino groups), this approach generally requires vigorous conditions, such as high temperature or strongly basic media, for bond formation to occur.

An alternative technique whereby highly reactive carbene or nitrene species are generated from inert precursors under less harsh photolytic, and sometimes thermolytic, conditions has also been investigated for application to dyeing and other surface modifying processes of various natural and synthetic polymers. The chemistry of cargenes and nitrenes is well documented, and these reactive entities are known to form covalent bonds with many types of functional groups. The application of these species to the surface modification or organic solids using different approaches both for the generation of the required carbenes or nitrenes, and for their reaction with the solid surface has been reported. Interestingly, although nitrenes (often generated from an azide or sulfonylazide precursor under photolytic or thermolytic conditions) are more stable, and therefore less reactive, than their carbene analogues, they have used much more widely for the dyeing of polymeric substrates.

French Patent No. 1 500 512 discloses allowing carbenes to come into contact with an organic solid. The preferred method for surface modification is to allow the volatilised carbene to come into contact with the polymer. Inherent in this approach, however, are limitations: only volatile (i.e. low molecular weight) carbenes, and those stable to relatively high temperatures, are applicable.

The application of carbenes generated from diazo compounds as suitable reactive dyes has been found to have important limitations, for example the ease of generation of the required diazo precursor (D. R. Braybrook et al., *J. Photochem. Photobiol A: Chem*, 1993, 70, 171) and the stability of the dye to the carbene generating process.

The present invention provides a process which may allow the surface functionalisation of materials which have hitherto been difficult to modify, for example glass or a variety of plastics. The process of the present invention may also allows greater flexibility than known processes in which a single carbene insertion step introduces the desired functionality. In addition, it is supposed that substrates which are dyed according to the process of the invention may exhibit superior wash-fastness to substrates dyed using existing processes due to a reduction in hydrolysable bonds on the surface of the substrate.

In a first aspect the present invention provides a process for the surface functionalisation of a polymeric substrate, which process comprises:
(a) contacting the substrate with a diarylcarbene precursor,
(b) generating a carbene reactive intermediate from the diarylcarbene precursor so that it reacts with the substrate to functionalise the surface, and
(c) further functionalising the activated substrate obtained in step (b).

In another aspect of the present invention steps (b) and (c) are combined.

The substrate may be any natural or synthetic polymeric substrate which is capable of reaction with a carbene reactive intermediate generated from a diarylcarbene precursor. The molecular weight of the polymeric substrate may be selected according to the desired processability of the final product. Typically the substrate is cotton, plastic, polystyrene, nylon, controlled pore glass, silica, an ethylene polymer or polytetrafluoroethylene.

By "diarylcarbene precursor", as used herein, is meant a diaryl species capable of venerating a carbene reactive intermediate under the reaction conditions. The diarylcarbene precursor must be such that the carbene reactive intermediate generated can react with the polymeric substrate and the activated substrate can be further functionalised.

Preferably the diarylcarbene precursor is a compound of formula I

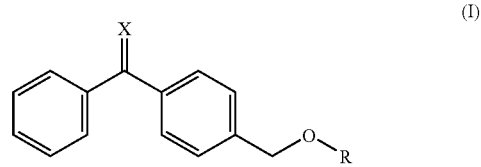

(I)

wherein
R is $Ar^1$ or $(CH_2)_m N(R^1)(R^2)$;
$Ar^1$ is

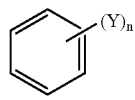

wherein Y is $C_1$ to $C_4$ alkoxy or $N(R^3)(R^4)$,
$R^3$ and $R^4$, which may be the same or different, are $C_1$ to $C_4$ alkyl,
n is an integer of 0 to 3;
$R^1$ is $C_1$ to $C_4$ alkyl;
$R^2$ is phenyl;
m is an integer of 1 to 4; and
X is $N_2$.

More preferably the diarylcarbene precursor is 4-([3,4-dimethoxyphenyl]oxymethyl)phenyl phenyl diazomethane 1, 4-([3-N,N-diethylaminophenyl]-oxymethyl)phenyl phenyl diazomethane 2 or 4-([N-ethyl-N-phenyl-2-aminoethyl] oxymethyl)phenyl phenyl diazomethane 3.

Typically the diaryl diazomethane compounds are stable and may be stored at 0° C. for extended periods.

Diarylcarbene precursors 1 and 2 may be prepared as shown in Scheme 1. 4-Bromomethylbenzophenone, which can be prepared according to D. D. Tanner et al. *J. Org. Chem.*, 1980, 45, 5177, is first coupled with the desired aryl alcohol. The resulting benzophenone may be converted to the hydrazone by treatment in refluxing ethanol overnight, followed by removal of the solvent and extraction into dichloromethane. Oxidation of the hydrazone to the corresponding diazo diarylcarbene precursor may conveniently be performed with mercuric oxide in ether.

Scheme 1

1′ $Y^1$ = OMe, $Y^2$ = OMe
2′ $Y^1$ = H, $Y^2$ = $NEt_2$ (i) $N_2H_4 \cdot H_2O$, EtOH
(ii) HgO, $Et_2O$, KOH, $NaSO_4$ 1 $Y^1$ = OMe, $Y^2$ = OMe
2 $Y^1$ = H, $Y^2$ = $NEt_2$ Diarylcarbene precursor 3 may be prepared similarly as shown in Scheme 2.

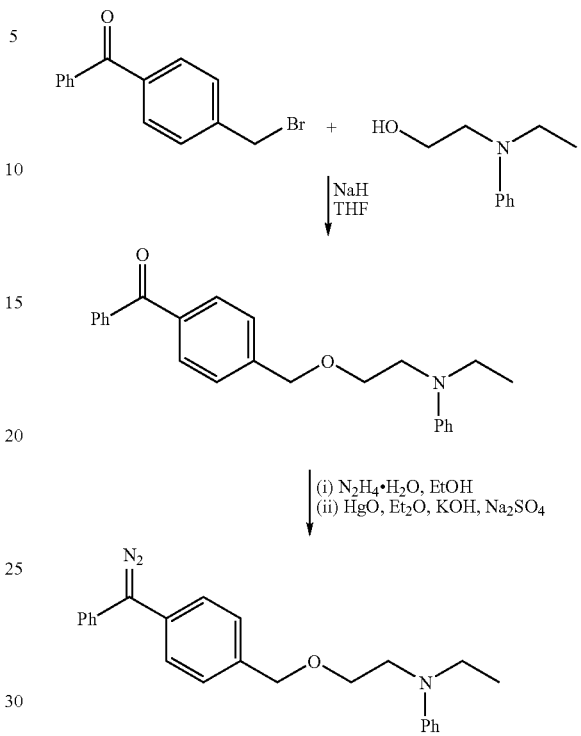

Scheme 2

(i) $N_2H_4 \cdot H_2O$, EtOH
(ii) HgO, $Et_2O$, KOH, $Na_2SO_4$

3

By "carbene reactive intermediate", as used herein, is meant a reactive species comprising a formally divalent carbon atom. The carbene reactive intermediate is generated from the diarylcarbene precursor by treatment under conditions which result in an irreversible covalent reaction with the substrate. Generally the carbene is generated by heating the substrate and pre-adsorbed diazo compound, or by irradiation. Typically, the substrate is heated for the time required for decolourisation. In one embodiment of the present invention part of the surface of the substrate is activated by selective heating or irradiation, for example by photoactivation using a laser. This may allow the controlled and selective modification of a two-dimensional polymer surface and may be useful in two-dimensional data storage such as CD data storage.

The activated substrate obtained in step (b) is further functionalised. By "functionalise", as used herein, is meant the introduction of a or another chemical functional group, which exhibits desirable physical or chemical properties, by irreversible covalent attachment. The activated substrate may be further functionalised by, for example, a dye, fluorescent brightener, UV-absorber, anti-static agent, flame retardant, surface finish, non-linear optical function, chelating function, electrically conducting function, magnetic function or polarising function.

The dye may be any suitable diazonium compound, for example a commercially available diazonium compound which may be selected to obtain the desired colour such as red, yellow, orange or blue. The colour may be altered in some cases by adjustment of pH of the final polymer sample by suitable treatment with acid or base. Examples of suitable diazonium compounds include those of formulae II, III or IV

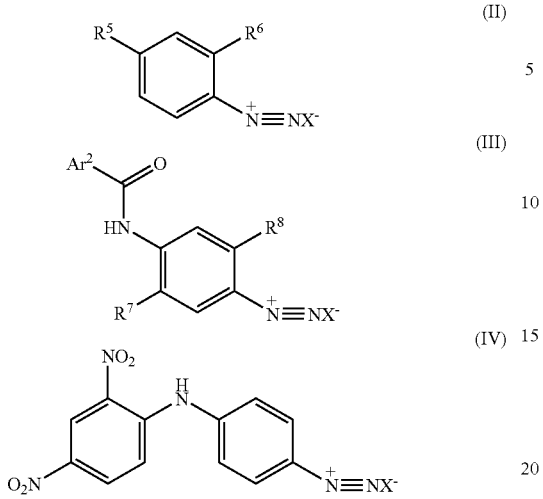

wherein $R^5$ and $R^6$, which may be the same or different, are $NO_2$ or $SO_3Na$;

$R^7$ and $R^8$, which may be the same or different, are $C_1$ to $C_4$ alkoxy, preferably methoxy;

$Ar^2$ is

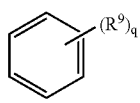

wherein $R^9$ is $C_1$ to $C_4$ alkyl and q is an integer of 0 to 3, preferably 0;

and

X is fluorine, chlorine, bromine or iodine.

The activated substrate may also be functionalised by, for example, introduction of a phthalocyanine functional group.

The process of the invention may find application in, for example, the dye industry, or combinatorial or polymer chemistry. More particularly the process of the present invention may find application in the preparation of immobilised catalysts, immobilised colours and dyes, photoelectric/solar cells, conducting (including photoelectric and semiconducting) polymers, magnetic polymers and optical recording and non-linear optical devices.

The process of the present invention may also be used in the preparation of biocidal or biostatic fabrics and plastics which have applications in, for example, water purification, medical and military clothing (where biocidal activity would help to minimise the transfer of infective agents or infections due to injury in the field) and surface anti-fouling of, for example, ship hulls, showers or tubing. The activated substrate obtained in step (b) of the process of the present invention may be functionalised by, for example, a chemical functional group comprising an antibiotic; a heavy metal such as silver, copper or zinc; a quaternary ammonium salt; a phosphonium salt; an oxidising agent such as an N-halamine or precursor thereof for example chloramine, chlorine, hydrogen peroxide or iodine; or a phenolic group. According to the process of the present invention the polymeric substrate may be, for example, a polymeric thread or a finished textile. The surface functionalised substrates prepared by the process of the present invention may be durable to repeated use and laundry, and may be regenerable. For example, the activated substrate obtained in step (b) may be functionalised using a urea hydroperoxide functional group which would be regenerable by treatment with hydrogen peroxide or an N-halamine functional group which would be regenerable with a chlorine solution such as hypochlorite bleach.

In a further aspect the present invention provides diarylcarbene precursors of formula I as defined above.

The Examples which follow further illustrate the present invention.

EXAMPLES

UV spectra were recorded on a Perkin Elmer 555 UV-visible spectrometer. IR spectra were obtained as Nujol mulls, or as liquid films, and were recorded on a Perkin Elmer 781 spectrophotometer: broad (br), weak (w), medium (m) and strong (s) bands are reported.

$^1$H NMR spectra were recorded on a Varian Gemini 200 MHz spectrometer using the solvents ($CDCl_3$ or $(CD_3)_2CO$) as internal standards. Multiplicities are recorded as s (singlet), d (doublet), t (triplet), q (quartet) and m (multiplet).

Mass spectra were recorded on VG Analytical Ltd. ZAB1F or MM30F mass spectrometers (probe ammonia chemical ionisation (CI $NH_3$), positive argon fast atom bombardment (FAB) and electron impact (EI)).

Melting points were recorded on a Stuart Scientific SMP1 melting point machine and are uncorrected.

Flash chromatography was performed using Merck silica gel. Eluants used were as indicated in the text and the following solvents were dried and purified before use according to standard procedures: dichloromethane was refluxed and distilled over calcium hydride, ethyl acetate was distilled and the first 20% of the distillate was discarded, petroleum ether (b.p. 60–80° C.) was distilled and the first 20% of the distillate was discarded. THF was refluxed and distilled over sodium benzophenone ketyl under an atmosphere of argon. When necessary, solvents were degassed using a water pump for 15 min. Thin layer chromatography was performed on Merck 60 $F_{254}$ Art.5554 precoated silica plates and product spots were visualised under UV conditions at 254 nm.

Benzophenone hydrazone was purchased from Aldrich.

Preparation of Diarylcarbene Precursors

General Method A for the Formation of Benzophenone Hydrazones.

The required benzophenone was refluxed in ethanol and hydrazine hydrate overnight. The solvent was removed in vacuo and the residue dissolved in DCM, washed with water, dried and concentrated under vacuum. The hydrazones, which were obtained as inseparable mixtures of the syn- and anti-isomers, were then used without further purification.

General Method B for the Formation of Diphenyl Diazomethanes

The required benzophenone hydrazone was dissolved in $Et_2O$ and stirred vigorously with yellow mercuric oxide (1.2 eq), sodium sulphate and saturated KOH in ethanol. Stirring was continued overnight and the mixture was filtered through Celite®. Excess solvent was removed under vacuum and the product was used without further purification.

4-Bromomethylbenzophenone

A stirred mixture of 4-methylbenzophenone (15.02 g, 76.6 mmol) and N-bromosuccinimide (14.2 g, 79.8 mmol) in CHCl$_3$ (100 cm$^3$) was heated under gentle reflux for 18 h with a 100 W bulb shining 2 cm from the flask. The reaction mixture was washed with water, dried (MgSO$_4$) and solvent was removed in vacuo). The resulting solid was then washed with Et$_2$O to remove any starting material to leave the product as a white solid (15.07 g, 71.5%, mp 110–112° C. (lit. 110–111°); $\delta_H$ (200 MHz; CDCl$_3$) 4.55 (2 H, s, CH$_2$Br), 7.46–7.70 (5 H, m, ArH), 7.80–7.9 (4 H, m, ArH o- to C=O); m/z 277 ([M$^{81}$Br+H]$^+$, 25%) and 275 ([M$^{79}$Br+H]$^-$, 25%), 197 (100%).

4-([3,4-Dimethoxyphenyl]oxymethyl)benzophenone 1'

To 3,4-dimethoxyphenol (1.69 g, 11 mmol) in THF was added NaH (60% dispersion in oil, 1.2 eq., 0.53 g) and stirring continued for 1 hour. 4-Bromomethyl benzophenone (3.01 g, 11 mmol) was then added to the solution and stirring continued for a further 24 hours. The solution was concentrated in vacuo, diluted with DCM, washed with citric acid (10% aq.), NaOH (1N) dried and solvent removed under vacuum. The residue was then purified by column chromatography, eluting with petrol (40–60):EtOAc 9:1 yielding the product as a white solid (2.58 g, 68%) (Found: C, 75.73; H, 5.96. C$_{22}$H$_{20}$O$_4$ requires C, 75.84; H, 5.79%), mp 74–75° C.; R$_f$=0.23 (Petrol:EtOAc 4:1); $\delta_H$ (250 MHz, CDCl$_3$) 3.82 (3 H, s, OCH$_3$), 3.86 (3 H, s, OCH$_3$), 5.10 (2 H, s, CH$_2$), 6.47 (1 H, dd, J 9, 1, ArH p- to OMe), 6.65 (1 H, d, J 1, ArH o- to 2 OR), 6.80 (1 H, d, J 9, ArH m- to 2 OR), 7.47–7.75 (5 H, m, ArH), 7.80–7.91 (4 H, m, ArH o- to C=O); $\delta_C$ (50.3 MHz, CDCl$_3$) 55.8 (OCH$_3$), 56.4 (OCH$_3$), 69.9 (CH$_2$O), 101.2 and 104.0 (ArCH o- to OCH$_2$Ar), 111.7 (ArCH m- to OCH$_2$Ar), 127.0, 128.3, 130.0 and 130.3 (ArCH o- and m- to C=O), 132.5 (ArCH p- to C=O), 137.0 and 137.5 (4° Ar CC=O), 141.9 (ArCCH$_2$O), 143.8 (4° ArCOCH$_2$), 149.9 (4° ArCOMe p- to OCH$_2$Ar), 153.0 (4° ArCOMe m- to OCH$_2$Ar), 196.3 (C=O); m/z (APCl$^+$) 349 ([M+H]$^+$, 100%).

4-([3,4-Dimethoxyphenyl]oxymethyl)benzophenone Hydrazone

The benzophenone 1' (1.52 g, 4.36 mmol) was reacted with hydrazine hydrate according to General Method A yielding the hydrazone as a yellow oil (1.50 g, 95%), $\delta_H$ (200 MHz, CDCl$_3$) 3.76, 3.77, 3.79 and 3.81 (6 H, 4* s, OCH$_3$), 4.91 and 5.03 (2 H, 2* s, CH$_2$), 5.47 (2 H, br s, NH$_2$), 6.40 and 6.46 ((1 H, 2*dd, J9, 1, ArH p- to OMe), 6.55 and 6.60 (1 H, 2* d, J 1, ArH o- to 2 OR), 6.68 and 6.73 (1 H, 2* d, J 9, ArH m- to 2 OR), 7.20–7.60 (9 H, m, ArH); $\delta_C$ (50.3 MHz, CDCl$_3$) 55.7 (OCH$_3$), 56.3 (OCH$_3$), 70.0 (CH$_2$O), 101.2 and 104.0 (ArCH o- to OCH$_2$Ar), 111.8 (ArCH m- to OCH$_2$Ar), 126.4, 126.5, 127.3, 128.0, 128.1, 128.5, 128.8, 128.9, 129.1 and 129.4 (ArCH o- and m- to C=N), 132.5 and 132.9 (ArCH p- to C=N), 136.9, 137.9, 138.2 and 138.4 (4* ArCC=N), 143.6 and 143.8 (4° Ar CCH$_2$O), 148.1 (4° ArCOCH$_2$), 149.8 and 149.9 (4° Ar COMe p- to OCH$_2$Ar), 153.2 (ArCOMe m- to OCH$_2$Ar); m/z (APCl$^+$) 363 ([M+H]$^+$, 100%).

4-([3,4-Dimethoxyphenyl]oxymethyl)phenyl Phenyl Diazomethane 1

The above benzophenone hydrazone (1.50 g, 4.14 mmol) was reacted with mercuric oxide and sodium sulphate according to General Method B yielding the diazomethane as a purple oil (1.35 g, 91%) (Found: C, 73.85; H, 5.33; N, 7.31. C$_{22}$H$_{20}$N$_2$O$_3$ requires C, 73.32; H, 5.59; N, 7.77%), $\nu^{max}$(film)cm$^{-1}$ 2038 (s), 1595 (m), 1511 (s); $\delta_H$ (500 MHz, CDCl$_3$) 3.85 (3 H, s, OCH$_3$), 3.87 (3 H, s, OCH$_3$), 5.02 (2 H, s, CH$_2$), 6.49 (1 H, dd, J 9, 1, ArH p- to OMe), 6.62 (1 H, d, J 1ARH o- to 2 OR), 6.80 (1 H, d, J 9, ArH m- to 2 OR), 7.16–7.49 (9 H, m, ArH); $\delta_C$ (125.8 MHz, CDCl$_3$) 55.8 (OCH$_3$), 56.4 (OCH$_3$), 70.2 (CH$_2$O), 101.2 and 104.0 (Ar CH o- to OCH$_2$Ar), 111.6 (ArCH m- to OCH$_2$Ar), 125.1, 125.2, 128.5 and 129.1 (ArCH o- and m- to C=N), 125.7 (ArCH p- to C=N), 129.3 and 129.4 (4° ArCC=N), 134.4 (4° ArCCH$_2$O), 143.6 (4° ArCOCH$_2$), 149.8 (4° ArCOMe p- to OCH$_2$Ar), 153.3 (4° ArCOMe m- to OCH$_2$Ar).

4-([3-N,N-Diethylaminophenyl]oxymethyl)benzophenone 2'

3-N,N-Diethylaminophenol (3.03 g, 18.4 mmol, 1.2 eq) in THF (20 cm$^3$) was treated with NaH (60% dispersion in oil, 524 mg, 13.1 mmol, 1.4 eq) and stirred at 20° C. for 1 hour. 4-Bromomethylbenzophenone (4.21 g, 15.3 mmol) was then added and stirring continued for 72 hours. Excess solvent was removed in vacuo and the residue diluted with DCM, washed with water and NaHCO$_3$ solution (sat.), dried (MgSO$_4$) and solvent removed under vacuum. The resulting oil was purified by flash chromatography, eluting with petroleum (bp 40–60° C.):EtOAc (9:1), to give the desired product as a yellow oil (4.29 g, 65%), R$_f$=0.51 (4:1, petrol: EtOAc) (Found: C, 79.99; H, 7.13; N, 5.23. C$_{24}$H$_{25}$NO$_2$ requires C, 80.19; H, 7.01; N, 3.90%; $\nu_{max}$ (film)/cm$^{-1}$ 1657 (s), 1610 (s); $\delta_H$ (500 MHz; CDCl$_3$) 1.17 (6 H, t, J 7, CH$_3$), 3.35 (4H, q, J 7, CH$_2$CH$_3$), 5.16 (2 H, s, ArCH$_2$O), 6.27–6.40 (3 H, m, ArH o- and p- to NEt$_2$), 7.15 (1 H, dd, J 7, 7, ArH m- to NEt$_2$), 7.45–7.66 (5 H, m, ArH), 7.80–7.89 (4 H, m, ArH o- to C=O); $\delta_C$ (125.8 MHz; CDCl$_3$) 12.6 (CH$_3$), 44.4 (NCH$_2$CH$_3$), 69.2 (ArCH$_2$O), 99.1, 100.8 and 105.4 (ArCH o- and p- to NEt$_2$), 127.0, 128.3, 130.0 and 130.4 (ArCH), 132.4 (ArCH p- to C=O), 136.9 and 137.6 (4° ArCC=O), 142.3 (4° ArCCH$_2$O), 149.2 ArCNEt$_2$), 159.9 (4° ArCOCH$_2$), 196.4 (C=O); m/z (APCl$^+$) 360 ([M+H]$^-$, 100%).

4-([3-N,N-Diethylaminophenyl]oxymethyl)benzophenone Hydrazone

The benzophenone 2' (1.76 g, 1.95 mmol) was reacted with hydrazine hydrate according to General Method A yielding the hydrazone as a colourless oil (1.31 g, 72%), (Found: C, 76.26; H, 7.30; N, 12.47. C$_{24}$H$_{27}$N$_3$O requires C, 77.18; H, 7.29; N, 11.25%); $\nu_{max}$(film)/cm$^{-1}$ 1605 (m); $\delta_H$ (200 MHz CDCl$_3$) 1.24–1.34 (6 H, m, CH$_3$), 3.39–3.54 (4 H, m, NCH$_2$CH$_3$), 5.16 and 5.24 (2 H, 2* s, ArCH$^2$O), 5.61 (2 H, br s, NNH$_2$), 6.45–6.52 (3 H, m, ArH o- and p- to NEt$_2$), 7.25–7.77 (10 H, m, ArH); $\delta_C$ (50.3 MHz; CDCl$_3$) 12.7 (CH$_3$), 44.5 (NCH$_2$CH$_3$), 69.6 and 69.7 (ArCH$_2$O), 99.4 and 99.5, 101.1 and 101.2, 105.6 and 105.7 (ArCH o- and p- to NEt$_2$), 126.8, 127.0, 127.7, 128.1, 128.4, 128.5, 128.9, 129.2, 129.5, 129.8, 130.3, 130.4, 132.8, 133.3, 137.7, 138.5, 138.7, 138.7 and 138.9 (ArCH, 4° ArCC=N and 4° ArCCH$_2$O), 148.8 (C=NNH$_2$), 149.5 (4° ArCNEt$_2$), 160.6 (4° ArCOCH$_2$); m/z (APCl$^+$) 374 ([M+H]$^+$, 15%), 209 (100), 195 (50), 178 (75).

4-([3-N,N-Diethylaminophenyl]oxymethyl)phenyl Phenyl Diazomethane 2

The above benzophenone hydrazone (1.30 g, 3.49 mmol) was stirred vigorously with yellow mercuric oxide (1.40 g, 6.5 mmol), anhydrous sodium sulphate (2.00 g, 14.1 mmol) in diethyl ether (33 cm$^3$) and saturated KOH in ethanol (1 cm$^3$) for 18 hours. The solution was filtered through Celite® and solvent removed in vacuo yielding the product as a red oil (1.22 g, 94%), $\nu_{max}$(film)/cm$^{-1}$ 2037 (s), 1612 (m); $\delta_H$ (200 MHz; CDCl$_3$) 1.27 (6 H, m, CH$_3$), 3.44 (4 H, m, NC H₂CH₃), 5.15 (2 H, s, ArCH₂O), 6.42–6.50 (3 H, m, ArH o- and p- to NEt₂), 7.21–7.55 (10 H, m ArH); δ$_C$ (50.3 MHz; CDCl₃) 12.8 (CH₃), 44.5 (NCH₂CH₃), 69.6 (ArCH₂O), 99.3, 101.0 and 105.5 (ArCH o- and p- to NEt₂), 128.2, 128.6, 128.7, 129.2 and 129.3 (ArCH o- and m- to C=N and ArCH m- to NEt₂), 130.0 (ArCH p- to C=N), 132.5 and 133.0 (4° ArCC=N), 135.0 (4° ArCCH₂O), 149.2 (4° Ar CNEt₂), 160.3 (4° ArCOCH₂).

4-([N-Ethyl-N-phenyl-2-aminoethyl]oxymethyl)benzophenone 2-(N-Ethylanilino)ethanol (3.03 g, 18.4 mmol, 1.2 eq) in THF (20 cm³) was treated with NaH (60% dispersion in oil, 524 mg, 13.1 mmol, 1.4 eq) and stirred at 20° C. for 1 hour. 4-Bromomethylbenzophenone (4.21 g, 15.3 mmol) was then added and stirring continued for 72 hours. Excess solvent was removed in vacuo and the residue diluted with DCM, washed with water and NaHCO₃ solution (sat.), dried (MgSO₄) and solvent removed under vacuum. The resulting oil was purified by flash chromatography, eluting with petroleum (bp 40–60° C.):EtOAc (9:1), to give the desired product as a yellow oil (4.36 g, 80%), R$_f$=0.54 (4:1, petrol: EtOAc) (Found: C, 78.34; H, 6.86; N, 5.29. C₂₄H₂₅NO₂ requires C, 80.19; H, 7.01; N, 3.90%); ν$_{max}$ (film/cm⁻¹ 1658 (s), 1598 (s), 1506 (s); δ$_H$ (200 MHz; CDCl₃) 1.22 (3 H, t, J 7, CH₃), 3.49 (2 H, q, J 7, CH₂CH₃), 3.58–3.79 (4 H, m, OCH₂CH₂N), 4.66 (2 H, s, ArCH₂O), 6.69–6.79 (3 H, m, ArH o- and p- to NR₂), 7.28 (2 H, dd, J 7, 7, ARH m- to NR₂), 7.46–7.68 (5 H, m, ArH), 7.80–7.88 (4 H, m, ArH o- to C=O); δ$_C$ (50.3 MHz; CDCl₃) 12.2 (CH₃),45.5 (N CH₂CH₃), 50.1 (NCH₂CH₂O), 68.5 (NCH₂CH₂O), 72.2 (Ar CH₂O), 111.8 (ArCH o- to NR₂), 115.8 (ArCH p- to NR₂), 127.0, 128.3, 129.3, 130.0 and 130.3 (ArCH o- and m- to C=O and ArCH m- to NR₂), 132.4 (ArCH p- to C=O), 136.8 and 137.7 (4° ArCC=O), 143.2 (4° ArCCH₂O), 147.7 (4° ArCNR₂), 196.4 (C=O); m/z (APCl⁺) 360 ([M+H]⁺, 30%); HRMS C₂₄H₂₆O₂N requires 360.1963; found 360.1963.

4-([N-Ethyl-N-phenyl-2-aminoethyl]oxymethyl)benzophenone Hydrazone

The above benzophenone (701 mg, 1.95 mmol) was reacted with hydrazine hydrate according to General Method A yielding the hydrazone as a colourless oil (710 mg, 97%), ν$_{max}$ (film)/cm⁻¹ 1598 (s), 1506 (s); δ$_H$ (500 MHz; CDCl₃) 1.27 and 1.31 (3 H, 2* t, J 7, CH₃), 3.52 and 3.57 (2 H, 2* q, J 7, CH₂CH₃), 3.60–3.87 (4 H, m, NCH₂CH₂O), 4.63 and 4.71 (2 H, 2* s, ArCH₂O), 5.57 (2 H, br s, NNH₂), 6.76–6.87 (3 H, m, ArH o- and p- to NR₂), 7.30–7.42 (7 H, m, ArH), 7.53–7.64 (4 H, m, ArH o- to C=N); δ$_C$ (125.8 MHz; CDCl₃) 12.0 (CH₃), 45.1 and 45.2 (NCH₂CH₃), 49.8 (N CH₂CH₂O), 67.8 and 68.1 (OCH₂CH₂N), 72.6 and 72.7 (Ar CH₂O), 111.5 and 111.6 (ArCH o- to NR₂), 115.5 and 115.6 (ArCH p- to NR₂), 126.2, 127.1, 127.7, 127.8, 128.1, 128.5, 128.6, 128.9, 129.0 and 129.1 (ArCH), 131.9 and 132.8 (4° ArCCH₂O), 137.7, 137.8, 138.3 and 138.9 (4° ArCC=N), 147.5 (4° ArCNR₂), 148.1 (C=NNH₂); m/z (APCl⁺) 374 ([M+H]⁺, 5%), 357 (5%), 209 (100%).

4-([N-Ethyl-N-phenyl-2-aminoethyl]oxymethyl)phenyl Phenyl Diazomethane 3

The above benzophenone hydrazone (701 mg, 1.88 mmol) was reacted with mercuric oxide and sodium sulphate according to General Method B yielding the diazomethane as a purple liquid (690 mg, 99%) (Found: C, 78.06; H, 6.89; N, 12.36. C₂₄H₂₅N₃O requires C, 77.60; H, 6.78; N, 11.31%); ν$_{max}$ (film)/cm⁻¹ 2037 (s), 1559 (m); δ$_H$ (500 MHz; CDCl₃) 1.26–1.32 (3 H, m, CH₃), 3.50–3.80 (6 H, m, NC H₂CH₃ and NCH₂CH₂O), 4.65 (2 H, s, ArCH₂O), 6.78–6.86 (3 H, m ArH o- and p- to NR₂), 7.28–7.65 (11 H, m ArH); δ$_C$ (125.8 MHz; CDCl₃) 12.1 (CH₃), 45.3 (NCH₂CH₃), 50.0 (NCH₂CH₂O), 67.9 (OCH₂CH₂N), 72.8 (ArCH₂O), 111.7 (ArCH o- to NR₂), 115.6 (ArCH p- to NR₂), 125.0, 125.5, 126.3, 128.3, 128.4, 128.7, 129.0, 129.1 and 129.2 (4° ArC and ArCH), 135.7 (4° ArCCH₂O), 147.7 (4° ArCNR₂); m/z (APCl⁻) 344 ([M–N₂]⁺, 20%), 209 (100).

Activation and Functionalisation of Substrates

2-Sulphonyl-4-nitrobenzene Diazonium Chloride (0.1M aq)

To a suspension of 2-amino-5-nitrobenzene sulphonic acid, sodium salt (2.40 g, 10 mmol) in iced water (50 cm³) and HCl (10 N, 5 cm³), NaNO₂ (1 M, 11 cm³) was slowly added and stirred vigorously for 5 minutes whilst maintaining the temperature at 0° C. The solution was made to pH 4 with sodium acetate and diluted to 100 cm³, the diazonium ion was then used without further purification at 0° C. within one hour of formation.

Functionalisation of Substrates

Solutions of the appropriate diazomethane or benzophenone (10–200 mg) in diethyl ether (1–2 ml), or pure ether, were applied to three samples of the appropriate polymeric substrate (100 mg–5 g) and the solvent allowed to evaporate at room temperature. One of these samples was taken out and kept aside. The rest of the substrate was then heated, in foil or conical flasks, with a heat gun for the time required to decolourise the substrate which had been treated with the diazocompound. Another sample from each batch of treated polymer was kept aside at this point. The remaining substrate was then moistened with ethanol (2 cm³) and a suspension of the diazonium salt (50 cm³, 0.1 M) was added and the mixture stirred overnight. The substrate was then removed, washed with water, hot water and soap, acetone, HCl (1N), NaOH (1N), water and acetone until no further colour leached out of the substrate into the liquid. The substrate was allowed to dry to obtain the final sample.

The use of compounds 1 to 3 for the modification of a range of substrates (cotton, controlled pore glass, polystyrene XAD-40, silica and nylon membrane) was investigated. Treating each substrate with the diazo compounds and heating to generate the corresponding carbene gave the surface-modified substrate; this effectively generated an activated polymer with the electron-rich aromatic residue attached (Scheme 3). Treatment of the activated polymer with the diazonium salt derived from 2-amino-5-nitrobenzene sulphonic acid then gave the corresponding azo-dyed material.

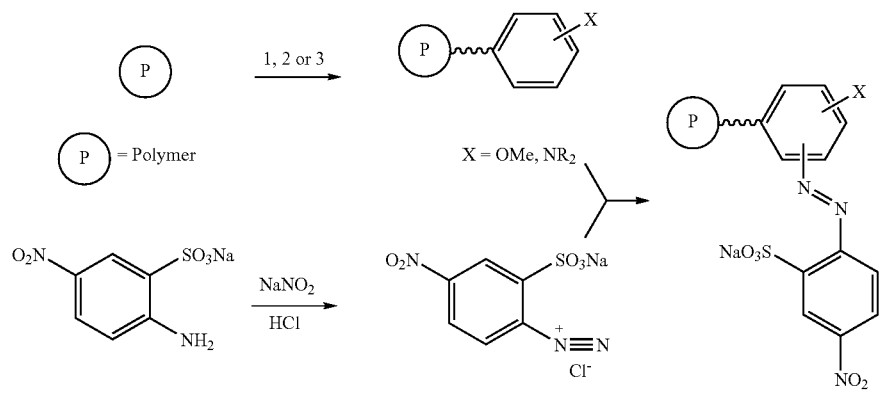

Scheme 3

For each substrate, nine controls were run simultaneously (each polymer was treated with the solvent only, the diazo compounds and their corresponding benzophenones, either just with the native polymer, with the native polymer and heating, and with the native polymer, heating and then adding the diazotisation reagent), in order to verify that any colouration that arose was due to irreversible bond formation, resulting from carbene insertion, and not merely physical adsorption, and the results are indicated in Table 1. The sample numbering scheme for the controls is indicated; samples 1–3 indicate that colouration is not derived simply from modification of the polymer alone in the heating and diazo treatment process, samples 4–6 indicate that the colouration derives from the diazo coupling reaction (shown in Scheme 3) but that this colour washes out, since there was no carbene insertion reaction when the benzophenones were used as the substrate. Samples 7–9 indicate that treatment with both the carbene and diazo coupling agents leads to irreversible colouration.

TABLE 1

DYEING OF VARIOUS SUBSTRATES WITH COMPOUNDS 1, 2 OR 3

| Polymer Treatment | Functionalising Compound | | |
|---|---|---|---|
| | Ether Solvent only | Benzophenone | Diphenyldiazomethane 1, 2 or 3 |
| Native Polymer | 1 | 4 | 7 |
| After Heating | 2 | 5 | 8 |
| After Diazotization and washing | 3 | 6 | 9 |

COTTON: Mercerised Woven Cotton

| | Sample Number | | | | | | | | |
|---|---|---|---|---|---|---|---|---|---|
| Compound | 1 | 2 | 3 | 4 | 5 | 6 | 7 | 8 | 9 |
| 1 | 0 | 0 | 0 | 0 | 0 | + | ++ | + | ++ |
| 2 | 0 | 0 | 0 | 0 | 0 | + | ++ | + | +++ |
| 3 | 0 | 0 | 0 | 0 | 0 | + | ++ | + | +++ |

TABLE 1-continued

POLYSTYRENE: Amberlite XAD-4 Non-ionic Polymeric Adsorbant (ex Aldrich Cat No 21, 648-8)

| | Sample Number | | | | | | | | |
|---|---|---|---|---|---|---|---|---|---|
| Compound | 1 | 2 | 3 | 4 | 5 | 6 | 7 | 8 | 9 |
| 1 | 0 | 0 | 0 | 0 | 0 | ++ | ++ | ++ | +++ |
| 2 | 0 | 0 | 0 | 0 | 0 | +++ | ++ | + | +++++ |
| †3 | 0 | 0 | 0 | 0 | 0 | +++ | ++ | + | +++++ |

POLYAMIDE: Hybond N (ex Amersham Life Science Cat. No. RPN203N)

| | Sample Number | | | | | | | | |
|---|---|---|---|---|---|---|---|---|---|
| Compound | 1 | 2 | 3 | 4 | 5 | 6 | 7 | 8 | 9 |
| 1 | 0 | 0 | 0 | 0 | 0 | + | ++ | + | ++ |
| 2 | 0 | 0 | 0 | 0 | 0 | + | ++ | + | ++++ |
| 3 | 0 | 0 | 0 | 0 | 0 | + | ++ | + | ++++ |

CONTROLLED PORE GLASS: (ex CPG Inc)

| | Sample Number | | | | | | | | |
|---|---|---|---|---|---|---|---|---|---|
| Compound | 1 | 2 | 3 | 4 | 5 | 6 | 7 | 8 | 9 |
| 1 | 0 | 0 | 0 | n/a | n/a | n/a | n/a | n/a | n/a |
| 2 | 0 | 0 | 0 | n/a | n/a | n/a | n/a | n/a | n/a |
| 3 | 0 | 0 | 0 | 0 | 0 | + | ++ | + | ++++ |

FLASH SILICA: (ex Merck)

| | Sample Number | | | | | | | | |
|---|---|---|---|---|---|---|---|---|---|
| Compound | 1 | 2 | 3 | 4 | 5 | 6 | 7 | 8† | 9 |
| 1 | 0 | 0 | 0 | 0 | 0 | + | ++ | + | +++ |
| 2 | 0 | 0 | 0 | 0 | 0 | + | ++ | + | +++++ |
| 3 | 0 | 0 | 0 | 0 | 0 | + | ++ | + | ++++ |

Scale:

| Colourless | | | | | Black |
|---|---|---|---|---|---|
| 0 | +++ | +++ | +++ | ++++ | ++++ |

†No heat was required for generation of the carbene

The invention claimed is:

1. A diaryl precursor of formula I:

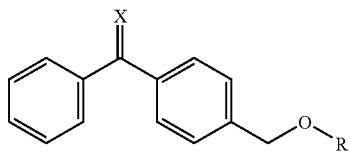

wherein
R is $Ar^1$ or $(CH_2)_m N(R^1)(R^2)$,
$Ar^1$ is

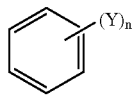

wherein Y is $C_1$ to $C_4$ alkoxy or $N(R^3)(R^4)$,
$R^3$ and $R^4$, which may be the same or different, are $C_1$ to $C_4$ alkyl,
n is an integer of 0 to 3,
$R^1$ is $C_1$ to $C_4$ alkyl,
$R^2$ is phenyl,
m is an integer of 1 to 4 and
X is $N_2$.

2. A precursor according to claim 1 wherein R is N-ethyl-N-phenyl-2-aminoethyl, 3,4-dimethoxyphenyl or 3-N,N-diethyl-aminopropyl.

3. 4-([3,4-dimethyoxyphenyl]oxymethyl)phenyl phenyl diazomethane.

4. 4-([3-N,N-diethylaminophenyl]oxymethyl)phenyl phenyl diazomethane.

5. 4-([N-ethyl-N-phenyl-2-aminoethyl]oxymethyl)phenyl phenyl diazomethane.

* * * * *

UNITED STATES PATENT AND TRADEMARK OFFICE
CERTIFICATE OF CORRECTION

PATENT NO. : 7,034,129 B2 Page 1 of 1
APPLICATION NO. : 10/741288
DATED : April 25, 2006
INVENTOR(S) : Mark G. Moloney et al.

It is certified that error appears in the above-identified patent and that said Letters Patent is hereby corrected as shown below:

On the Title page, add item -- (30) Foreign Application Priority Data November 3, 1998 (03.11.98) (GB) 9824023.7 --.

Signed and Sealed this

Twenty-fourth Day of June, 2008

JON W. DUDAS
*Director of the United States Patent and Trademark Office*